United States Patent [19]

Shida et al.

[11] Patent Number: 5,001,275
[45] Date of Patent: Mar. 19, 1991

[54] BENZYL ETHER COMPOUND AND PROCESS FOR PRODUCING THE SAME

[75] Inventors: Takafumi Shida; Yoshikazu Kubota; Isao Ichinose, all of Iwaki, Japan

[73] Assignee: Kureha Kagaku Kogyo Kabushiki Kaisha, Tokyo, Japan

[21] Appl. No.: 433,421

[22] Filed: Nov. 7, 1989

[30] Foreign Application Priority Data

Feb. 5, 1987 [JP] Japan .................................. 62-25240
Feb. 5, 1987 [JP] Japan .................................. 62-25241

[51] Int. Cl.$^5$ ............................................ C07C 43/00
[52] U.S. Cl. .................................................. 568/583
[58] Field of Search ................. 568/583; 564/442, 443

[56] References Cited

U.S. PATENT DOCUMENTS

| | | | |
|---|---|---|---|
| 4,348,223 | 9/1982 | Grove | 71/118 |
| 4,543,425 | 9/1985 | Konrad et al. | 564/442 |
| 4,625,062 | 11/1986 | Nagata et al. | 564/442 |

OTHER PUBLICATIONS

Chemical Abstracts, vol. 83, No. 11, Abstract No. 92302q.
Chemical Abstract Ninth Collective Index, vol. 76–85, Abstract No. 56190-97-7.
The Journal of the Chemical Society, vol. 1954, p. 4129, (1954).
Ceskoslovenska Farmacie, vol. 30, p. 184 (1981).
Analytical Chemistry, vol. 54, p. 529 (1982).

Primary Examiner—Bruce Gray
Attorney, Agent, or Firm—John P. White

[57] ABSTRACT

Disclosed herein are a benzyl ether compound represented by the general formula (I):

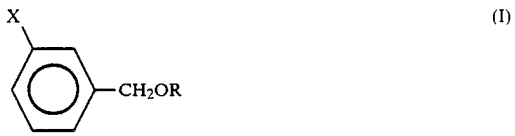

wherein R represents a branched alkyl group of 4 to 8 carbon atoms, a cycloalkyl group of 4 to 8 carbon atoms, an alkyl group of 1 to 3 carbon atoms having an alicyclic group of 3 to 7 carbon atoms, an aralkyl group of 7 to 9 carbon atoms, an alkyl group of 2 to 4 carbon atoms having an alkoxy group of 1 to 4 carbon atoms, an unsaturated alkyl group of 3 to 6 carbon atoms, a straight-chain alkyl group of 2 to 8 carbon atoms which has been substituted by 1 to 15 fluorine atoms, or a branched alkyl group of 3 to 8 carbon atoms which has been substituted by 1 to 15 fluorine atoms, and X represents a nitro group or an amino group, provided that when X is a nitro group, R is neither an aralkyl group nor an ethyl group substituted by fluorine atom(s), a process for producing the same.

19 Claims, No Drawings

BENZYL ETHER COMPOUND AND PROCESS FOR PRODUCING THE SAME

This is a continuation of application Ser. No. 042,164, filed Apr. 24, 1987, abandoned.

BACKGROUND OF THE INVENTION:

The present invention relates to a benzyl ether compound which is useful as an intermediate compound of a 1,2,4-triazole-3-carboxamide compound having a weed killing effect (herbicidal effect) and a process for producing the same. More particularly, the present invention relates to a benzyl ether compound which is used as an intermediate compound of a 1,2,4-triazole-3-carboxamide compound which is an active ingredient of a herbicide, and which is represented by the general formula (I):

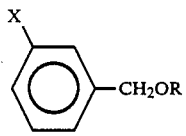
(I)

wherein R represents a branched alkyl group of 4 to 8 carbon atoms, a cycloalkyl group of 4 to 8 carbon atoms, an alkyl group of 1 to 3 carbon atoms having an alicyclic group of 3 to 7 carbon atoms, an aralkyl group of 7 to 9 carbon atoms, an alkyl group of 2 to 4 carbon atoms having an alkoxy group of 1 to 4 carbon atoms, an unsaturated alkyl group of 3 to 6 carbon atoms, a straight-chain alkyl group of 2 to 8 carbon atoms which has been substituted by 1 to 15 fluorine atoms, or a branched alkyl group of 3 to 8 carbon atoms which has been substituted by 1 to 15 fluorine atoms, and X represents a nitro group or an amino group, provided that when X is a nitro group, R is neither an aralkyl group nor an ethyl group substituted by fluorine atom(s);

a process for preparing a nitrobenzene compound represented by the general formula (IV):

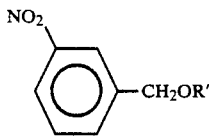
(IV)

wherein R' represents a branched alkyl group of 4 to 8 carbon atoms, a cycloalkyl group of 4 to 8 carbon atoms, an alkyl group of 1 to 3 carbon atoms having an alicyclic group of 3 to 7 carbon atoms, an alkyl group of 2 to 4 carbon atoms having an alkoxy group of 1 t 4 carbon atoms, an unsaturated alkyl group of 3 to 6 carbon atoms, a straightchain alkyl group of 2 to 8 carbon atoms which has been substituted by 1 to 15 fluorine atoms, or a branched alkyl group of 3 to 8 carbon atoms which has been substituted by 1 to 15 fluorine atoms, which comprises reacting a 3-nitrobenzyl chloride represented by the general formula (II):

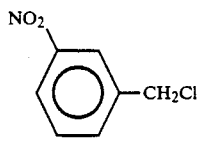
(II)

with an alcohol represented by the general formula (III):

R'OH     (III)

wherein R' is as defined above, in an aprotic polar solvent in the presence of an accepter of hydrogen chloride; and a process for producing an aniline compound represented by the general formula (V):

(V)

wherein R represents a branched alkyl group of 4 to 8 carbon atoms, a cycloalkyl group of 4 to 8 carbon atoms, an alkyl group of 1 to 3 carbon atoms having an alicyclic group of 3 to 7 carbon atoms, an aralkyl group of 7 to 9 carbon atoms, an alkyl group of 7 to 9 carbon atoms, an alkyl group of 2 to 4 carbon atoms having an alkoxy group of 1 to 4 carbon atoms, an unsaturated alkyl group of 3 to 6 carbon atoms, a straight-chain alkyl group of 2 to 8 carbon atoms which has been substituted by 1 to 15 fluorine atoms, or a branched alkyl group of 3 to 8 carbon atoms which has been substituted by 1 to 15 fluorine atoms, which comprises reacting a 3-nitrobenzyl chloride represented by the general formula (II):

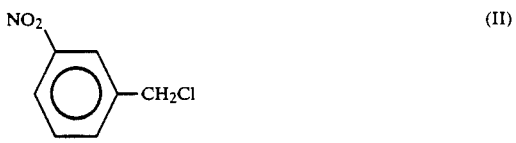
(II)

with an alcohol represented by the following general formula (III'):

ROH     (III')

wherein R is as defined above, in an aprotic polar solvent in the presence of an accepter of hydrogen chloride, and reducing the thus obtained nitrobenzene compound.

A nitrobenzene compound represented by the general formula (IV'):

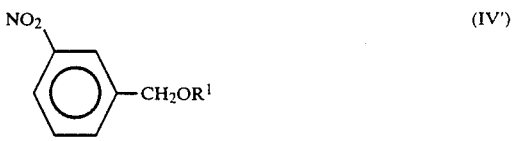
(IV')

wherein $R^1$ represents a methyl group, an ethyl group, an n-propyl group, an n-butyl group, an n-pentyl group or an n-hexyl group, and an aniline compound represented by the general formula (V'):

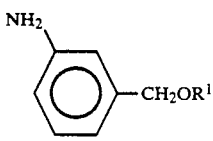

wherein R¹ represents a methyl group, an ethyl group, an n-propyl group, an n-butyl group, an n-pentyl group or an n-hexyl group, are known.

For example, compounds represented by the formula (IV') and (V') wherein R¹ is a methyl group are described in The Journal of the Chemical Society, vol. 1954 (1954) page 4127, in which a compound represented by the formula (IV') wherein R¹ is a methyl group is synthesized at a yield of 72% by heating 3-nitrobenzyl chloride in a methanol dissolved metallic sodium therein, and a compound represented by the formula (V') wherein R¹ is a methyl group is synthesized at a yield of 82% by reducing 1-(methoxymethyl)-3-nitrobenzene with iron-saline solution. The synthesis of compounds represented by the formula (IV') and (V') wherein R¹ is an ethyl group, an n-propyl group, an n-butyl group, an n-pentyl group or an n-hexyl group are described in Chekoslovenska Farmacie, vol. 30 (1981) page 184, in which the compounds represented by the formula (IV') are synthesized at a yield of 65 to 75% in the same manner as in the synthesis of the compound represented by the formula (IV') wherein R¹ is a methyl group, and the aniline compounds represented by the formula (V') are synthesized at a yield of 75 to 81% by reducing the corresponding nitrobenzene compounds.

As a compound having a branched alkyl group, a compound wherein R¹ is an i-propyl group is known. U.S. Pat. No. 4,348,223 (1982) discloses a compound represented by the formula (IV') wherein R¹ is an i-propyl group which is synthesized at a yield of 42% by heating 3-nitrobenzyl chloride with an aqueous solution of KOH in i-propanol and further a compound represented by the formula (V') wherein R¹ is an i-propyl group which is synthesized at a yield of 91% by catalytic reduction of the corresponding nitrobenzene compound.

Many compounds are known in which R¹ is a phenyl group. As a typical example, an unsubstituted phenyl group will be cited. By a process described in The Journal of the Chemical Society, vol. 1954 (1954) page 4573 a compound represented by the formula (IV') wherein R¹ is a phenyl group is synthesized at a yield of 60% by heating 3-nitrobenzyl bromide and phenol in methylethyl ketone in the presence of K₂CO₃, and the Journal of Pharmaceutical Sciences vol. 56 (1976) page 871 describes that a compound represented by the formula (V') wherein R¹ is a phenyl group is synthesized at a yield of about 50% by catalytic reduction of the corresponding nitrobenzene derivative.

A compound represented by the formula (IV') wherein R¹ is a benzyl group is described in The Journal of Organic Chemistry, vol. 51 (1986) page 2777 and a compound represented by the formula (IV') wherein R¹ is a propynyl group (-CH₂C≡CH) is described in Chemical Abstracts, vol. 83 No. 92302, but the detailed synthetic methods of those compounds are not described.

As a compound represented by the formula (IV') wherein R¹ is a fluoroalkyl group a compound represented by the formula (IV') wherein R¹ is a 2,2,2-trifluoroethyl group is known. A compound represented by the formula (IV') wherein R¹ is a 2,2,2-trifluoroethyl group described in Analytical Chemistry, vol. 54 (1982) page 529 is obtained at a yield of 95% by reacting 2,2,2-trifluorodiazoethane (CF₃CH=N⁺=N⁻) with 3-nitrobenzyl alcohol

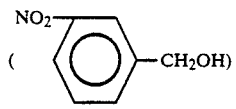

in fluoboric acid.

However, no prior publication discloses a compound represented by the formula (V) wherein R represents a branched alkyl group of 4 to 8 carbon atoms, a cycloalkyl group of 4 to 8 carbon atoms, an alkyl group of 1 to 3 carbon atoms having an alicyclic group of 3 to 7 carbon atoms, an aralkyl group of 7 to 9 carbon atoms, an alkyl group of 2 to 4 carbon atoms having an alkoxy group of 1 to 4 carbon atoms, an unsaturated alkyl group of 3 to 6 carbon atoms, or a straight-chain or branched alkyl group of 2 to 8 carbon atoms which has been substituted by 1 to 15 fluorine atoms; or a compound represented by the formula (IV) wherein R' represents a branched alkyl group of 4 to 8 carbon atoms, a cycloalkyl group of 4 to 8 carbon atoms, an alkyl group of 1 to 3 carbon atoms having an alicyclic group of 3 to 7 carbon atoms, an alkyl group of 2 to 4 carbon atoms having an alkoxy group of 1 to 4 carbon atoms, an unsaturated alkyl group of 3 to 6 carbon atoms, or a straight-chain or branched alkyl group of 3 to 8 carbon atoms which has been substituted by 1 to 15 fluorine atoms.

As a result of the present inventors' various researches to provide a 1,2,4-triazole-3-carboxamide compound having an excellent weed killing effect, represented by the formula (VI):

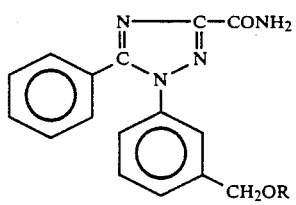

wherein R is as defined above, it has been found that a benzyl ether compound represented by the formula (I) is a useful compound as an intermediate compound of the 1,2,4-triazole-3-carboxamide compound represented by the formula (VI) as a herbicide, and on the basis of this finding, the present invention has been attained.

SUMMARY OF THE INVENTION

In a first aspect of the present invention, there is provided a benzyl ether compound represented by the general formula (I):

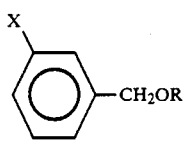 (I)

wherein R represents a branched alkyl group of 4 to 8 carbon atoms, a cycloalkyl group of 4 to 8 carbon atoms, an alkyl group of 1 to 3 carbon atoms having an alicyclic group of 3 to 7 carbon atoms, an aralkyl group of 7 to 9 carbon atoms, an alkyl group of 2 to 4 carbon atoms having an alkoxy group of 1 to 4 carbon atoms, an unsaturated alkyl group of 3 to 6 carbon atoms, a straight-chain alkyl group of 2 to 8 carbon atoms which has been substituted by 1 to 15 fluorine atoms, or a branched alkyl group of 3 to 8 carbon atoms which has been substituted by 1 to 15 fluorine atoms, and X represents a nitro group or an amino group, provided that when X is a nitro group, R is neither an aralkyl group nor an ethyl group substituted by fluorine atom(s).

In a second aspect of the present invention, there is provided a process for preparing a nitrobenzene compound which is represented by the general formula (IV):

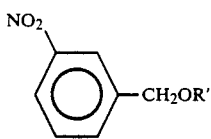 (IV)

wherein R' represents a branched alkyl group of 4 to 8 carbon atoms, a cycloalkyl group of 4 to 8 carbon atoms, an alkyl group of 1 to 3 carbon atoms having an alicyclic group of 3 to 7 carbon atoms, an alkyl group of 2 to 4 carbon atoms having an alkoxy group of 1 to 4 carbon atoms, an unsaturated alkyl group of 3 to 6 carbon atoms, a straight-chain alkyl group of 2 to 8 carbon atoms which has been substituted by 1 to 15 fluorine atoms, or a branched alkyl group of 3 to 8 carbon atoms which has been substituted by 1 to 15 fluorine atoms, which comprises reacting a 3-nitrobenzyl chloride represented by the general formula (II):

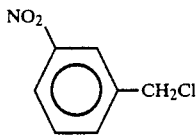 (II)

with an alcohol represented by the general formula (III):

R'OH (III)

wherein R' is as defined above in an aprotic polar solvent in the presence of an accepter of hydrogen chloride.

In a third aspect of the present invention, there is provided a process for producing an aniline compound represented by the general formula (V):

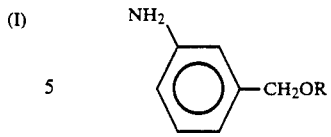 (V)

wherein R represents a branched alkyl group of 4 to 8 carbon atoms, a cycloalkyl group of 4 to 8 carbon atoms, an alkyl group of 1 to 3 carbon atoms having an alicyclic group of 3 to 7 carbon atoms, an aralkyl group of 7 to 9 carbon atoms, an alkyl group of 2 to 4 carbon atoms having an alkoxy group of 1 to 4 carbon atoms, an unsaturated alkyl group of 3 to 6 carbon atoms, a straight-chain alkyl group of 2 to 8 carbon atoms which has been substituted by 1 to 15 fluorine atoms, or a branched alkyl group of 3 to 8 carbon atoms which has been substituted by 1 to 15 fluorine atoms, which comprises reacting a 3-nitrobenzyl chloride represented by the general formula (II):

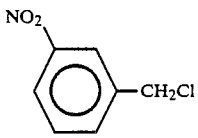 (II)

with an alcohol represented by the following general formula (III'):

ROH (III')

wherein R is as defined above in an aprotic polar solvent in the presence of an accepter of hydrogen chloride, and reducing the thus obtained nitrobenzene compound.

DETAILED DESCRIPTION OF THE INVENTION:

A benzyl ether compound according to the present invention is a compound represented by the general formula (I):

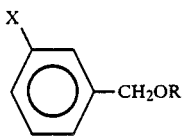 (I)

wherein R represents a branched alkyl group of 4 to 8 carbon atoms, a cycloalkyl group of 4 to 8 carbon atoms, an alkyl group of 1 to 3 carbon atoms having an alicyclic group of 3 to 7 carbon atoms, an aralkyl group of 7 to 9 carbon atoms, an alkyl group of 2 to 4 carbon atoms having an alkoxy group of 1 to 4 carbon atoms, an unsaturated alkyl group of 3 to 6 carbon atoms, a straight-chain alkyl group of 2 to 8 carbon atoms which has been substituted by 1 to 15 fluorine atoms, or a branched alkyl group of 3 to 8 carbon atoms which has been substituted by 1 to 15 fluorine atoms, and X represents a nitro group or an amino group, provided that when X is a nitro group, R is neither an aralkyl group nor an ethyl group substituted by fluorine atom(s).

A preferred compound represented by the general formula (I) is a compound in which R is a branched alkyl group of 4 to 6 carbon atoms, an alkyl group of 1 to 2 carbon atoms having an alicyclic group of 3 to 6 carbon atoms, an aralkyl group of 7 carbon atoms, an alkyl group of 2 carbon atoms having an alkoxy group of 4 carbon atoms, an unsaturated alkyl group of 3 to 6 carbon atoms, a straight-chain alkyl group of 2 to 8 carbon atoms which has been substituted by 3 to 12 fluorine atoms, or a branched alkyl group of 3 to 8 carbon atoms which has been substituted by 3 to 12 fluorine atoms. More specifically, a preferred compound is exemplified by the following compounds:

1-(2-methylbutoxy)methyl-3-nitrobenzene
1-(3-methylbutoxy)methyl-3-nitrobenzene
1-(2,2-dimethylpropoxy)methyl-3-nitrobenzene
1-(cyclohexylmethoxy)methyl-3-nitrobenzene
1-(2,2,3,3,3-pentafluoropropoxy)methyl-3-nitrobenzene
1-(2,2,3,4,4,4-hexafluorobutoxy)methyl-3-nitrobenzene
1-(2,2,3,3,4,4,4-heptafluorobutoxy)methyl-3-nitrobenzene
1-(2,2,3,3,4,4,5,5-octafluoropentoxy)methyl-3-nitrobenzene
3-[(2-methylbutoxy)methyl]aniline
3-[(3-methylbutoxy)methyl]aniline
3-[(2,2-dimethylpropoxy)methyl]aniline
3-[(cyclohexylmethoxy)methyl]aniline
3-[2,2,2-trifluoroethoxy)methyl]aniline
3-[(2,2,3,3,3-pentafluoropropoxy)methyl]aniline
3-[(2,2,3,4,4,4-hexafluorobutoxy)methyl]aniline
3-[(2,2,3,3,4,4,4-heptafluorobutoxy)methyl]aniline
3-[(2,2,3,3,4,4,5,5-octafluoropentoxy)methyl]aniline.

A nitrobenzene compound represented by the general formula (IV):

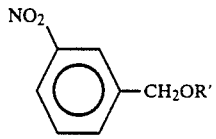
(IV)

wherein R' represents a branched alkyl group of 4 to 8 carbon atoms, a cycloalkyl group of 4 to 8 carbon atoms, an alkyl group of 1 to 3 carbon atoms having an alicyclic group of 3 to 7 carbon atoms, an alkyl group of 2 to 4 carbon atoms having an alkoxy group of 1 to 4 carbon atoms, an unsaturated alkyl group of 3 to 6 carbon atoms, a straightchain alkyl group of 2 to 8 carbon atoms which has been substituted by 1 to 15 fluorine atoms, or a branched alkyl group of 2 to 8 carbon atoms which has been substituted by 1 to 15 fluorine atoms, is produced by reacting a 3-nitrobenzyl chloride represented by the general formula (II):

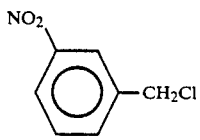
(II)

with an alcohol represented by the general formula (III):

R'OH      (III)

wherein R' is as defined above, in an aprotic polar solvent in the presence of an accepter of hydrogen chloride.

An aniline compound represented by the general formula (V):

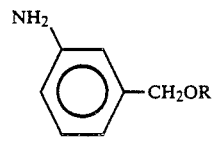
(V)

wherein R represents a branched alkyl group of 4 to 8 carbon atoms, a cycloalkyl group of 4 to 8 carbon atoms, an alkyl group of 1 to 3 carbon atoms having an alicyclic group of 3 to 7 carbon atoms, an aralkyl group of 7 to 9 carbon atoms, an alkyl group of 2 to 4 carbon atoms having an alkoxy group of 1 to 4 carbon atoms, an unsaturated alkyl group of 3 to 6 carbon atoms, a straight-chain alkyl group of 2 to 8 carbon atoms which has been substituted by 1 to 15 fluorine atoms, or a branched alkyl group of 3 to 8 carbon atoms which has been substituted by 1 to 15 atoms, is produced by reacting a 3-nitrobenzyl chloride represented by the general formula (II):

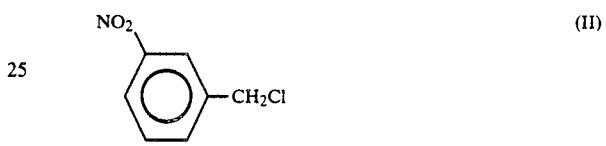

with an alcohol represented by the following general formula (III'):

ROH      (III')

wherein R is as defined above, in an aprotic polar solvent in the presence of an accepter of hydrogen chloride, and reducing the thus obtained nitrobenzene compound.

When an alcohol represented by the formula (III) and (III') is reacted with 3-nitrobenzyl chloride represented by the formula (II), 1 to 5 equivalents of alcohol per 3-nitrobenzyl chloride is generally used.

As the aprotic polar solvent, a ketone solvent such as acetone and methylethyl ketone; an ether solvent such as tetrahydrofuran, dioxane, ethylene glycol dimethyl ether and diethylene glycol dimethyl ether; a nitrile solvent such as acetonitrile; an amide solvent such as dimethylformamide, dimethylacetamide, N-methylpyrrolidone and hexamethylphosphoramide; and a sulfur containing solvent such as dimethyl sulfoxide and sulfolane may be exemplified.

As the accepter of hydrogen chloride, an inorganic base such as sodium hydroxide, potassium hydroxide sodium carbonate, potassium carbonate, sodium hydride and metallic sodium; and an organic base such as triethylamine, pyridine and N,N-dimethylaniline may be exemplified.

The reaction temperature is not lower than the melting point of a solvent or in the range of −10° to 150° C., preferably not lower than the melting point of a solvent or in the range of 10° to 80° C.

The reaction is generally completed in 0.1 to 10 hours, and thereafter the product is separated by recovering the solvent or pouring water into the reaction mixture.

A conventional reducing method may be adopted to reduce a nitrobenzene compound represented by the formula (IV).

For example, a method of reacting iron, zinc, tin, etc. or ferrous salt, stannous salt, etc. in an acid, alkaline or neutral solvent may be used. In this case, as the acid solvent, hydrochloric acid, sulfuric acid and acetic acid may be exemplified As the alkaline solvent, alcoholic sodium hydroxide, ethanolic potassium hydroxide, or aqueous ammonia may be exemplified. As the neutral solvent, an aqueous solution with salt, ammonium chloride, or potassium chloride dissolved therein may be exemplified.

As another method, a method of reacting a sulfide such as sodium sulfide, ammonium sulfide, sodium polysulfide and sodium hydrosulfide in an organic solvent such as ethanol and dioxane, an aqueous solvent thereof, or aqueous ammonia may be used. As still another method, a method of reacting colloidal sulfur in an organic solvent such as methanol, ethanol, acetone and dioxane or an aqueous solvent thereof under the coexistence of sodium hydroxide, potassium hydroxide and ammonia may be used.

Still another method, a method of using hydrazine as a hydrogen donor may be adopted In this case, a high boiling solvent such as diethylene glycol is used as a solvent, reduction is carried out in ethanol in which ferric salt and active carbon coexist, or reduction is carried out in ethanol in which palladium carbon exists.

Furthermore, a catalytic reduction method may also be adopted. In this case, reduction is carried out in ethanol or acetic acid by pressurizing hydrogen to a pressure ranging from a normal pressure to 5 atm in the presence of Raney nickel, palladium carbon, platinum oxide or the like as the catalyst.

The examples of the novel compounds obtained in this manner will be shown together with the physical and chemical properties and the synthetic yields thereof in Tables 1 and 2. Tables 3 and 4 show the results of the elemental analysis of these novel compounds.

According to a process of the present invention, the intended products are obtained at a yield of 80 to 96% except when there is a steric hindrance by using a secondary alcohol and a primary alcohol having a ramification at a carbon at the 2-position as an alcohol represented by the formula (III). Thus, this process is superior to a conventional method.

TABLE 1

Physical and Chemical Properties of

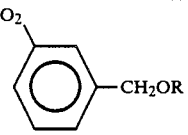

| Compound No. | R | Synthesizing Method* Yield | Boiling point °C. (mm Hg) | Nuclear magnetic resonance spectrum (CDCl$_3$, δ, ppm, 60 MHz) |
|---|---|---|---|---|
| 1 | CH$_3$<br>\|<br>CH$_3$CH$_2$CHCH$_2$— | Method A<br>65.8 | 119-20<br>(0.18) | 0.90(3H, t, 7.3Hz), 0.94(3H, d, 6.8Hz), 1.17, 1.49, 1.70(each 1H, m), 3.30(1H, dd, 6.4, 9.0Hz), 3.38 (1H, dd, 6.4, 9.0Hz), 4.58(2H, s), 7.51(1H, t, 7.8Hz), 7.67(1H, d, 7.8Hz), 8.14(1H, d, 7.8Hz), 8.20(1H, s)** |
| 2 | CH$_3$\\<br>　　CHCH$_2$CH$_2$—<br>CH$_3$/ | Method A<br>90.1 | 116-7<br>(0.08) | 0.92(6H, d, 6Hz), 1.0-2.0(3H, m), 3.75(2H, t, 6Hz), 4.56(2H, s), 7.3-8.3(4H, m) |
| 3 | CH$_3$<br>\|<br>CH$_3$C—CH$_2$—<br>\|<br>CH$_3$ | Method A<br>68.5 | 97-8<br>(0.5) | 0.97(9H, s), 3.13(2H, s), 4.56(2H, s), 7.3-8.3(4H, m) |
| 4 | ⟨H⟩—CH$_2$— | Method A<br>65.9 | 128-30<br>(0.04) | 0.8-1.85(11H, m), 3.07(2H, d, 6.4Hz), 4.57(2H, s), 7.51(1H, t, 7.8Hz), 7.67(1H, d, 7.8Hz), 8.13(1H, d, 7.8Hz), 8.20(1H, s)** |
| 5 | CH$_3$(CH$_2$)$_3$O(CH$_2$)$_2$— | Method A<br>82.3 | 126-7<br>(0.04) | 0.92(3H, t, 7.3Hz), 1.37(2H, 6-plet, 7.3Hz), 1.59(2H, tt, 7.3, 6.8Hz), 3.48(2H, t, 6.8Hz), 3.66(4H, m), 4.67 (2H, s), 7.51(1H, t, 7.8Hz), 7.69(1H, d, 7.8Hz), 8.14(1H, d, 7.8Hz), 8.23(1H, s)** |
| 6 | CH$_2$=CHCH$_2$— | Method A<br>83.2 | 100-1<br>(0.17) | 4.09(2H, dt, 5.4, 1.5Hz), 4.61(2H, s), 5.25(1H, dq, 10.7, 1.5Hz), 5.34(1H, dq, 17.1, 1.5Hz), 5.97(1H, ddt, 17.1, 10.7, 5.4), 7.52(1H, t, 7.8), 7.69(1H, d, 7.8), 8.15(1H, d, 7.8), 8.22(1H, s)** |
| 7 | CHF$_2$CF$_2$CH$_2$— | Method A<br>96.9 | 83-4<br>(0.9) | 3.93(2H, t, 13Hz), 4.73(2H, s), 5.97(1H, tt, 54,5), 7.3-8.3(4H, m) |
| 8 | CF$_3$CF$_2$CH$_2$— | Method B<br>83.0 | 86-7<br>(0.6) | 4.00(2H, t, 13Hz), 4.76(2H, s), 7.3-8.2(4H, m) |
| 9 | CF$_3$\\<br>　　CH—<br>CF$_3$/ | Method B<br>33.5 | 83-4<br>(0.25) | 4.30(1H, 7-plet, 6Hz), 5.00(2H, s), 7.3-8.2(4H, m) |
| 10 | CF$_3$CHFCF$_2$CH$_2$— | Method A<br>96.8 | 121-3<br>(0.3) | 3.6-4.2(2H, m), 4.63(2H, s), 5.00(1H, d, 6-plet, 50, 7Hz), 7.5-8.4(4H, m) |

TABLE 1-continued

Physical and Chemical Properties of

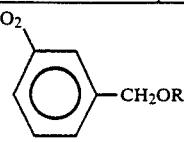

| Compound No. | R | Synthesizing Method* Yield | Boiling point °C. (mm Hg) | Nuclear magnetic resonance spectrum (CDCl$_3$, δ, ppm, 60 MHz) |
|---|---|---|---|---|
| 11 | CF$_3$(CF$_2$)$_2$CH$_2$— | Method A 94.9 | 149–51 (9) | 4.03(2H, tt, 14, 1.5Hz), 4.77(2H, s), 7.3–8.3(4H, m) |
| 12 | CHF$_2$(CF$_2$)$_3$CH$_2$— | Method B 95.0 | 122–4 (0.4) | 3.93(2H, tt, 14, 1.5Hz), 4.67(2H, s), 5.97(1H, tt, 52, 5Hz), 7.2–8.5(4H, m) |
| 13 | CHF$_2$(CF$_2$)$_5$CH$_2$— | Method A 87.6 | 123–4 (0.6) | 4.20(2H, tt, 14, 1.5Hz), 4.83(2H, s), 5.97(1H, tt, 52, 5Hz), 7.3–8.3(4H, m) |

(Note)
*Synthetic Method:
Method A: KOH/dimethylformamide
Method B: NaH/hexamethylphosphoramide
**Measured by a 250 MHz device

TABLE 2

Physical and Chemical Properties of

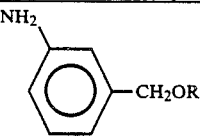

| Compound No. | R | Reducing Method Yield % | Boiling point °C. (mm Hg) | Nuclear magnetic resonance spectrum (CDCl$_3$, δ, ppm, 60 MHz) |
|---|---|---|---|---|
| 14 | CH$_3$<br>\|<br>CH$_3$CH$_2$CHCH$_2$— | Method A 97.9 | 102–4 (0.19) | 0.88(3H, t, 7.3Hz), 0.91(3H, d, 6.8Hz), 1.13, 1.48, 1.71(each 1H, m), 3.22(1H, dd, 6.3, 9.0Hz), 3.31(1H, dd, 6.3, 9.0Hz), 3.65(2H, bs), 4.41(2H, s), 6.60(1H, dd, 7.8, 2.0Hz), 6.69(1H, d, 2.0Hz), 6.72(1H, d, 7.8Hz), 7.12(1H, t, 7.8Hz)** |
| 15 | CH$_3$\<br>　　CHCH$_2$CH$_2$—<br>CH$_3$/ | Method A 97.1 | 105–6 (0.19) | 0.88(6H, d, 6Hz), 1.1–2.2(3H, m), 3.5(2H, bs), 3.47 (2H, t, 6Hz), 4.36(2H, s), 6.5–7.2(4H, m) |
| 16 | CH$_3$<br>\|<br>CH$_3$C—CH$_2$—<br>\|<br>CH$_3$ | Method B 96.2 | 98–100 (0.3) | 0.90(9H, s), 3.07(2H, s), 3.53(2H, s), 4.30(2H, s), 6.3–7.3(4H, m) |
| 17 | cyclohexyl-CH$_2$— | Method A 91.1 | 137–8 (0.18) | 0.93(2H, m), 1.21(3H, m), 1.68(6H, m), 3.25(2H, d, 6.4Hz), 3.65(2H, bs), 4.41(2H, s), 6.60(1H, dd, 7.8, 2.0Hz), 6.69(1H, d, 2.0Hz), 6.71(1H, d, 7.8Hz), 7.12 (1H, t, 7.8Hz)** |
| 18 | C$_6$H$_5$-CH$_2$— | Method B 92.5 | 140–2 (0.4) | 3.5(2H, bs), 4.40, 4.50(each 2H, s), 6.4–7.4(4H, m), 7.3(5H, s) |
| 19 | CH$_3$(CH$_2$)$_3$O(CH$_2$)$_2$— | Method A 96.9 | 123–5 (0.1) | 0.91(3H, t, 7.3Hz), 1.37(2H, 6-plet, 7.3Hz), 1.58(2H, 5-plet, 7.3Hz), 3.47(2H, t, 7.3Hz), 3.60(4H, s), 3.66(2H, bs), 4.49(2H, s), 6.60(1H, dd, 7.8, 1.5), 6.70(1H, d, 1.5Hz) 6.72(1H, d, 7.8Hz), 7.12(1H, t, 7.8Hz)** |
| 20 | CH$_2$=CHCH$_2$— | Method C 72.4 | 88–90 (0.1) | 3.66(2H, bs), 4.02(2H, dt, 5.4, 1.5Hz), 4.44(2H, s), 5.20(1H, dq, 10.3, 1.5Hz), 5.31(1H, dq, 17.1, 1.5Hz), 5.96(1H, ddt, 17.1, 10.3, 5.4Hz), 6.61(1H, dd, 7.8, 1.5Hz), 6.71(1H, d, 1.5Hz), 6.72(1H, d, 7.8Hz), 7.13 (1H, t, 7.8Hz)** |
| 21 | CF$_3$CH$_2$— | Method B 95.3 | 135–7 (18) | 3.50(2H, bs), 3.70(2H, q, 9Hz), 4.47(2H, s), 6.5–7.2(4H, m) |
| 22 | CHF$_2$CF$_2$CH$_2$— | Method B 96.2 | 86–8 (0.3) | 3.50(2H, bs), 3.73(2H, t, 12Hz), 4.47(2H, s), 5.90(1H, tt, 54, 5Hz), 6.4–7.3(4H, m) |

TABLE 2-continued

Physical and Chemical Properties of

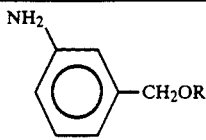

| Compound No. | R | Reducing Method Yield % | Boiling point °C. (mm Hg) | Nuclear magnetic resonance spectrum (CDCl$_3$, δ, ppm, 60 MHz) |
|---|---|---|---|---|
| 23 | CF$_3$CF$_2$CH$_2$— | Method D 77.1 | 86-7 (0.6) | 3.60(2H, s), 3.85(2H, t, 13Hz), 4.55(2H, s), 7.47-7.62(4H, m) |
| 24 | CF$_3$\\CH—/CF$_3$ | Method B 90.7 | 113-5 (0.3) | 3.60(2H, bs), 4.07(1H, 7-plet, 6Hz), 4.67(2H, s), 6.3-7.3(4H, m) |
| 25 | CF$_3$CHFCF$_2$CH$_2$— | Method B 94.5 | 91-3 (0.2) | 3.4-4.1(2H, m), 3.53(2H, bs), 4.48(2H, s), 5.02(1H, d, 6-plet, 50, 7Hz), 6.4-7.3(4H, m) |
| 26 | CF$_3$(CF$_2$)$_2$CH$_2$— | Method B 97.8 | 82-4 (0.3) | 3.57(2H, s), 3.87(2H, tt, 13, 2Hz), 4.55(2H, s), 6.5-7.4(4H, m) |
| 27 | CHF$_2$(CF$_2$)$_3$CH$_2$— | Method B 92.3 | 104-5 (0.35) | 3.50(2H, s), 3.83(2H, tt, 14, 2Hz), 4.50(2H, s), 6.00(1H, tt, 52, 6Hz), 6.4-7.3(4H, m) |
| 28 | CHF$_2$(CF$_2$)$_5$CH$_2$— | Method B 94.8 | 121-2 (0.9) | 3.47(2H, s), 3.87(2H, t, 14Hz), 4.53(2H, s), 5.97(1H, tt, 52, 5Hz), 6.4-7.3(4H, m) |

(Note)
*Reducing method:
Method A: N$_2$H$_4$/10% Pd—C/EtOH
Method B: N$_2$H$_4$/FeCl$_3$—C/EtOH
Method C: Colloidal sulfur/NaOH/Acetone-MeOH
Method D: Fe/Acetic acid
**Measured by a 250 MHz device

TABLE 3

Elemental Analysis of

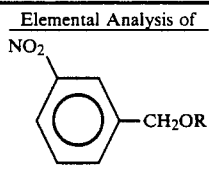

| Compound No. | Molecular formula | Found Calculated | C (%) | H (%) | N (%) |
|---|---|---|---|---|---|
| 1 | C$_{12}$H$_{17}$NO$_3$ | Found | 64.74 | 7.48 | 6.26 |
| | | Calculated | 64.56 | 7.67 | 6.27 |
| 2 | C$_{12}$H$_{17}$NO$_3$ | Found | 64.40 | 7.85 | 6.26 |
| | | Calculated | 64.56 | 7.67 | 6.27 |
| 3 | C$_{12}$H$_{17}$NO$_3$ | Found | 64.67 | 7.54 | 6.27 |
| | | Calculated | 64.56 | 7.67 | 6.27 |
| 4 | C$_{14}$H$_{19}$NO$_3$ | Found | 67.61 | 7.88 | 5.55 |
| | | Calculated | 67.45 | 7.68 | 5.62 |
| 5 | C$_{13}$H$_{19}$NO$_4$ | Found | 61.77 | 7.60 | 5.34 |
| | | Calculated | 61.64 | 7.56 | 5.53 |
| 6 | C$_{10}$H$_{11}$NO$_3$ | Found | 62.10 | 5.89 | 7.20 |
| | | Calculated | 62.17 | 5.74 | 7.25 |
| 7 | C$_{10}$H$_9$F$_4$NO$_3$ | Found | 44.89 | 3.51 | 5.41 |
| | | Calculated | 44.96 | 3.40 | 5.24 |
| 8 | C$_{10}$H$_8$F$_5$NO$_3$ | Found | 42.16 | 2.83 | 4.73 |
| | | Calculated | 42.12 | 2.83 | 4.91 |
| 9 | C$_{10}$H$_7$F$_6$NO$_3$ | Found | 39.69 | 2.14 | 4.78 |
| | | Calculated | 39.62 | 2.33 | 4.62 |
| 10 | C$_{11}$H$_9$F$_6$NO$_3$ | Found | 41.85 | 2.80 | 4.45 |
| | | Calculated | 41.65 | 2.86 | 4.42 |
| 11 | C$_{11}$H$_8$F$_7$NO$_3$ | Found | 39.22 | 2.23 | 4.02 |
| | | Calculated | 39.42 | 2.41 | 4.18 |
| 12 | C$_{12}$H$_9$F$_8$NO$_3$ | Found | 39.29 | 2.39 | 3.90 |
| | | Calculated | 39.25 | 2.47 | 3.81 |
| 13 | C$_{14}$H$_9$F$_{12}$NO$_3$ | Found | 36.19 | 2.05 | 2.80 |
| | | Calculated | 35.99 | 1.94 | 3.00 |

TABLE 4

Elemental Analysis of

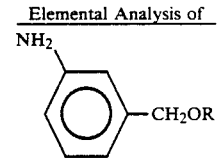

| Compound No. | Molecular formula | Found Calculated | C (%) | H (%) | N (%) |
|---|---|---|---|---|---|
| 14 | C$_{12}$H$_{19}$NO | Found | 74.50 | 9.78 | 7.44 |
| | | Calculated | 74.57 | 9.91 | 7.25 |
| 15 | C$_{12}$H$_{19}$NO | Found | 74.76 | 9.96 | 7.15 |
| | | Calculated | 74.57 | 9.91 | 7.25 |
| 16 | C$_{12}$H$_{19}$NO | Found | 74.60 | 10.09 | 7.12 |
| | | Calculated | 74.57 | 9.91 | 7.25 |
| 17 | C$_{14}$H$_{21}$NO | Found | 76.70 | 9.81 | 6.56 |
| | | Calculated | 76.67 | 9.65 | 6.39 |
| 18 | C$_{14}$H$_{15}$NO | Found | 78.87 | 7.28 | 6.63 |
| | | Calculated | 78.84 | 7.09 | 6.57 |
| 19 | C$_{13}$H$_{21}$NO$_2$ | Found | 70.12 | 9.58 | 6.25 |
| | | Calculated | 69.92 | 9.48 | 6.27 |
| 20 | C$_{10}$H$_{13}$NO | Found | 73.73 | 7.83 | 8.41 |
| | | Calculated | 73.59 | 8.03 | 8.58 |
| 21 | C$_9$H$_{10}$F$_3$NO | Found | 52.53 | 4.73 | 6.68 |
| | | Calculated | 52.69 | 4.91 | 6.83 |
| 22 | C$_{10}$H$_{11}$F$_4$NO | Found | 50.53 | 4.75 | 6.02 |
| | | Calculated | 50.64 | 4.67 | 5.90 |
| 23 | C$_{10}$H$_{10}$F$_5$NO | Found | 46.96 | 4.14 | 5.29 |
| | | Calculated | 47.07 | 3.95 | 5.49 |
| 24 | C$_{10}$H$_9$F$_6$NO | Found | 43.94 | 3.52 | 5.30 |
| | | Calculated | 43.97 | 3.32 | 5.13 |
| 25 | C$_{11}$H$_{11}$F$_6$NO | Found | 46.20 | 4.02 | 4.68 |
| | | Calculated | 46.00 | 3.86 | 4.88 |
| 26 | C$_{11}$H$_{10}$F$_7$NO | Found | 43.17 | 3.50 | 4.78 |
| | | Calculated | 43.29 | 3.30 | 4.59 |
| 27 | C$_{12}$H$_{11}$F$_8$NO | Found | 42.78 | 3.49 | 4.03 |
| | | Calculated | 42.74 | 3.29 | 4.15 |
| 28 | C$_{14}$H$_{11}$F$_{12}$NO | Found | 38.65 | 2.58 | 3.32 |
| | | Calculated | 38.46 | 2.54 | 3.20 |

A novel benzyl ether compound represented by the general formula (I) which is obtained at a high yield according to the present invention is useful as a synthetic material of a herbicide of 1,2,3-triazole-3-carboxamide represented by the formula (IV) which is described in U.S. patent application Ser. No. 918111 (filed Oct. 14, 1986).

The synthetic reaction is shown in the scheme (I). A nitrobenzene compound represented by the general formula (IV) is reduced thereby obtaining an aniline compound represented by the general formula (V). With the aniline compound, nitrous acid is reacted thereby obtaining a diazonium salt, and then 2-phenyl-2-oxazolin-5-one is reacted with the thus obtained diazonium salt to obtain a hydrazone compound represented by the general formula (VII). After ammonia is reacted with the thus obtained hydrazone compound, dehydrating and ring closure thereof are carried out thereby obtaining a 1,2,4-triazole-3-carboxamide compound represented by the general formula (VI).

The advantages as a herbicide of the compound represented by the general formula (VI) are described in detail in U.S. patent application Ser. No. 918111 (filed Oct. 14, 1986).

cooled in a water bath and stirred strongly. The reaction temperature was elevated to 43° C. and thereafter gradually restored to room temperature. After the mixture was stirred for 7 hours at room temperature, the reaction was completed.

The solid material of the reaction mixture was filtered out and after the pH of the filtrate was adjusted to 2 with dilute hydrochloric acid, the excess alcohol and dimethylformamide were distilled off. The residue was dissolved in a mixed solvent of 450 ml of n-hexane and 50 ml of ethyl acetate, successively washed with 1N-HCl and saturated saline solution, and dried by magnesium sulfate.

After distilling off the solvent, 185.2 g (90.1%) of the objective product having a boiling point of 116° to 117° C. (0.08 mmHg) was obtained by fractional distillation.

EXAMPLE 2

Synthesis of 1-(2,2,3,3,4,4,4-heptafluorobutoxy)methyl-3-nitrobenzene (Compound No. 11)

100.0 g (0.58 mol) of 3-nitrobenzyl chloride and 128.3 g (0.62 mol, 1.05 equivalents) of 2,2,3,3,4,4,4-heptafluorobutanol(purity: 96%) were dissolved in 300 ml of

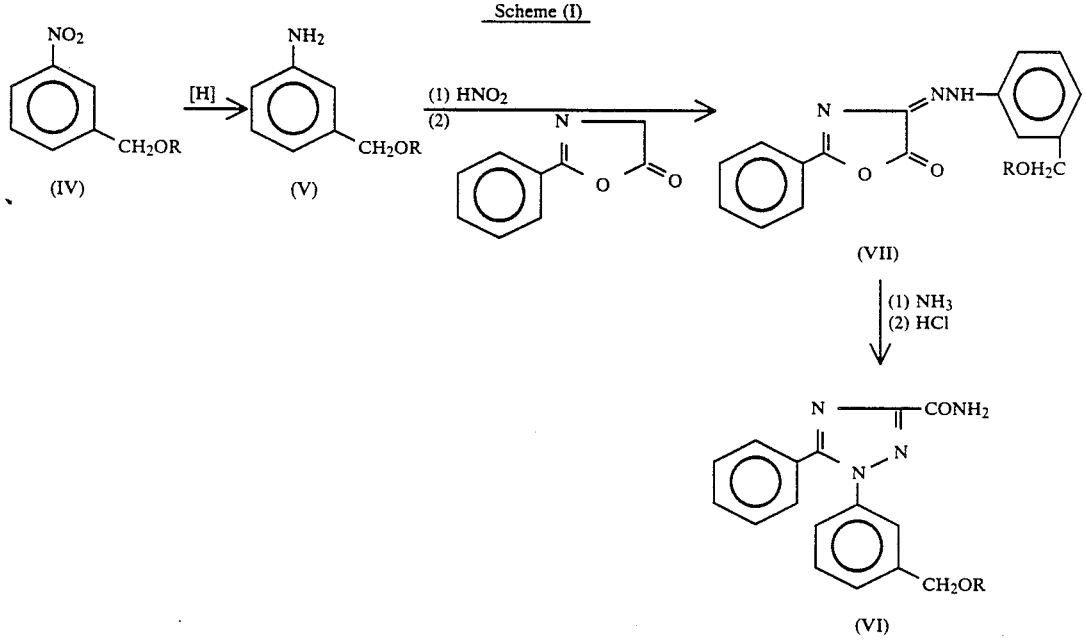

Scheme (I)

The present invention will be more precisely explained while referring to Examples as follows.

However, the present invention is not restricted to Examples under mentioned. From the foregoing description, one skilled in the art can easily ascertain the essential characteristics of the present invention, and without departing from the spirit and scope thereof, can make various changes and modifications of the invention to adapt it to various usages and conditions.

EXAMPLE 1

Synthesis of 1-(3-methylbutoxy)methyl-3-nitrobenzene (Compound No. 2)

158.1 g (0.92 mol) of 3-nitrobenzyl chloride was dissolved in a mixture of 500 ml (4.59 mol, 5 equivalents) of 3-methyl-1-butanol and 140 ml of dimethylformamide. To the resultant mixture 78 g (1.39 mol, 1.5 equivalents) of KOH pellets were added while the mixture was being dimethylformamide. To the resultant mixture 49.0 g (0.88 mol, 1.5 equivalents) of KOH pellets were added while the mixture was being cooled in a water bath. The reaction temperature is elevated to 43° C. and thereafter gradually restored to room temperature, and the reaction was completed after 30 minutes.

The reaction mixture was diluted with 300 ml of water and after the pH was adjusted to 2 with diluted hydrochloric acid, extraction was carried out two times with a mixed solvent of 250 ml of benzene and 100 ml of hexane. The organic layer was washed with 2N-HCl and saturated saline solution successively, and thereafter was dried by sodium sulfate. After distilling off the solvent, 185.4 g (94.9%) of the objective product having a boiling point of 149° to 151° C. (9 mmHg) was obtained by fractional distillation.

EXAMPLE 3

Synthesis of
1-(2,2,3,3,3-pentafluoropropoxy)methyl-3-nitrobenzene
(Compound No. 8)

9.6 g (0.24 mol) of sodium hydride (60% content in mineral oil) was washed with dried n-hexane. Thereafter, it was dispersed into 300 ml of hexamethylphosphoramide. 36.5 g (0.24 mol) of 2,2,3,3,3-pentafluoropropanol was carefully added thereto while being cooled in a water bath to change it into sodium salt. 39.5 g (0.23 mol) of 3-nitrobenzyl chloride dissolved in 50 ml of hexamethylphosphoramide was next added dropwise to the solution.

After 30 minutes from the completion of the dropping, the reaction was completed. The reaction mixture was poured into 200 ml of water. After the pH was adjusted to 2 with diluted hydrochloric acid, extraction was carried out two times with 150 ml of benzene. The organic layer was washed with 100 ml of 6N-HCl three times, washed with water and saturated saline solution successively, and thereafter was dried over anhydrous sodium sulfate.

After distilling off the solvent, 54.5 g (83.0%) of the objective product having a boiling point of 86° to 87° C. (0.6 mmHg) was obtained by fractional distillation.

EXAMPLE 4

Synthesis of 3-[(3-methylbutoxy)methyl]aniline
(Compound No 15)

130 g (0.58 mol) of 1-(3-methylbutoxy)methyl-3-nitrobenzene (Compound No. 2) obtained in Example 1 was dissolved in 150 ml of ethanol, and 0.6 g of 10% palladium carbon was added thereto. While the mixture was being stirred, 89 ml (1.84 mol) of hydrazine hydrate was added dropwise thereto at a rate which prevents violent foaming. The mixture was refluxed for 3 hours in a water bath after the completion of the dropping, thereby completing the reaction.

After the reaction liquid was left to cool, the catalyst was filtered out and the liquid was washed with ethanol. The filtrate was concentrated and dissolved in 300 ml of dichloromethane. The solution was successively washed with an aqueous solution of 10% sodium carbonate and saturated saline solution, and was dried by anhydrous potassium carbonate.

After distilling off the solvent, 109.2 g (97.1%) of the intended product having a boiling point of 105° to 106° C. (0.19 mmHg) was obtained by fractional distillation of the residue.

EXAMPLE 5

Synthesis of
3-[(2,2,3,3,4,4,4-heptafluorobutoxy)methyl]aniline
(Compound No. 26)

180 g (0.54 mol) of 1-(2,2,3,3,4,4,4-heptafluorobutoxy)methyl-3-nitrobenzene (Compound No. 11) obtained in Example 2 was dissolved in 500 ml of ethanol, and the mixture was refluxed for 30 minuted after adding 7.9 g of $FeCl_3.6H_2O$ and 12.5 g of activated carbon thereto. While the mixture was being stirred, 100 g (2.00 mol) of hydrazine hydrate was added dropwise thereto so as not to cause violent foaming. The mixture was refluxed for 2 hours after the completion of the dropping, thereby completing the reaction. After the reaction mixture was left to cool, the reaction mixture was filtered through a Celite layer and washed with ethanol. The filtrate was concentrated and dissolved in 500 ml of benzene. The solution was successively washed with water and saturated saline solution and was dried by anhydrous sodium sulfate.

After distilling off the solvent, 160.2 g (97.8%) of the objective product having a boiling point of 82° to 84° C. (0.3 mmHg) was obtained by fractional distillation of the residue.

EXAMPLE 6

Synthesis of
3-[(2,2,3,3,3-pentafluoropropoxy)methyl]aniline
(Compound No. 23)

51.3 g (0.18 mol) of 1-(2,2,3,3,3-pentafluoropropoxy)-methyl-3-nitrobenzene (Compound No. 8) obtained in Example 3 was dissolved in 70 ml of acetic acid, and was added dropwise to 150 ml of acetic acid with 70 g of iron powder dispersed therein for 2 hours so as to maintain the reaction temperature at 70° to 80° C. After the completion of the dropping, the reaction mixture was heated to 80° C. for 30 minutes in a water bath. After the reaction mixture was left to cool, the reaction mixture was filtered and washed with acetic acid and benzene successively. The filtrate was concentrated and neutralized with an aqueous solution of sodium bicarbonate. Benzene was added thereto and the mixture was filtered again to completely remove the iron salt. The organic layer was washed with saturated saline solution and was dried by anhydrous sodium sulfate.

After distilling off the solvent, 35.4 g (77.1%) of the objective product having a boiling point of 86° to 87° C. (0.6 mmHg) was obtained by fractional distillation. Reference Examples: Synthesis of 1-[3-[(3-methylbutoxy)methyl]phenyl]-5-phenyl-1H-1,2,4-triazole-3-carboxamide (compound represented by the general formula (VI) wherein R is a 3-methylbutyl group)

(1) Synthesis of
4-[3-[(3-methylbutoxy)methyl]phenylhydrazono]-2-phenyl-2-oxazolin-5-one (compound represented by the general formula (VII) wherein R is a 3-methylbutyl group)

109.2 g (0.566 mol) of 3-[(3-methylbutoxy)methyl]aniline (Compound No. 15) obtained in Example 4 was dissolved in a mixture of 140 ml of acetic acid and 140 ml of concentrated hydrochloric acid and was cooled in an icesalt bath. To the solution 39.4 g (0.571 mol) of sodium nitrite dissolved in 100 ml of water was added dropwise at a rate so as to maintain the reaction temperature at not higher than 0° C., thereby obtaining a diazonium salt solution.

101.6 g (0.567 mol) of hippuric acid was dispersed in 330 ml (3.49 mol) of acetic anhydride and heated to 80° C. in a water bath for about 20 minutes, thereby obtaining a solution of 2-phenyl-2-oxazolin-5-one. The thus obtained solution was cooled to $-20°$ C. in a dry ice acetone bath. Thereto 93 g of anhydrous sodium acetate was added and the diaszonium salt solution prepared in advance was added to the mixture with vigorous stirring at a rate so as to maintain the reaction temperature at not higher than $-10°$ C. After the completion of the dropping, the reaction mixture was held at $-10°$ C. for 2 hours, and thereafter was stirred for 5 hours in an ice bath. Further, the mixture was stirred for one night in a water bath, and thereafter 1.5 l of water was added to filter out a yellow precipitate, which was washed with water to obtain the objective product.

(2) Synthesis of 1-[3-[(3-methylbutoxy)methyl]phenyl]-5-phenyl-1H-1,2,4-triazole-3-carboxamide The wet crystals of the hydrazone derivative obtained in the reaction in Reference Example (1) was dispersed in 1.3 l of acetone, and 97 ml (0.75 mol) of concentrated aqueous ammonia was added thereto with vigorous stirring. After 1 hour, 78 ml (0.81 mol) of concentrated hydrocloric acid was added to adjust the pH to 2, and the mixture was heated to 50° C. for 30 minutes in a water bath.

After acetone was distilled off, the residue was extracted two times with 300 ml of benzene, and the organic layer was dried by anhydrous sodium sulfate. The crude crystals obtained by distilling off benzene were recrystallized from n-hexane-dichloromethylene to obtain 128.1 g (yield: 69.1%) of the objective product.

The melting point was from 118° to 120° C., which was the same as that of 118° to 120° C. of a product described in Japanese Patent Application No. 61-239092 (1986)

TEST EXAMPLE

A compound according to the present invention was induced to a final compound (compound represented by the general formula (VI)) having a weed killing activity and described in Japanese Patent Application No. 61-239092 (1986). The final compound was used in the form of a wettable powder. The weed killing activity of each of the final compounds is shown below.

(1) Preparation of a herbicidal composition of a wettable powder
  Final compound 50 parts
  Lignin sulfonate 5 parts
  Alkyl sulfonate 3 parts
  Diatomaceous earth 42 parts (2) Application test to the soil before germination of plants:

Soil was filled into a planter (650×210×220 cm) in a state of a crop field. The field was sowed with a predetermined amount of seeds of various test plants, and were thereafter covered with soil. A wettable powder of the above-described herbicidal composition was diluted and was so adjusted that the compound as the effective component was equivalent to 20 g/are. The dilute solution was uniformly dispersed on the surface of the soil, and the plants were grown and controlled in a greenhouse.

Herbicidal effect of the compound on each plant was evaluated on the basis of the following creteria after 25 days from the above-described treatment.

Evaluation Criteria

Killing effect (Herbicidal effect)

0—No weed killing effect (herbicidal effect)
1—not more than 30% of herbicidal effect
2—31 to 50 % of herbicidal effect
3—51 to 70 % of herbicidal effect
4—71 to 90 % of herbicidal effect
5—91 to 100 % of herbicidal effect.

(3) The results of the tests are shown in Table 5.

TABLE 5

Weed Killing Activity (Herbicidal Activity) of Final Compound Represented by the General Formula (VI)

| Test plant | Final compound No.* | | | | | | | | | | | | | | |
|---|---|---|---|---|---|---|---|---|---|---|---|---|---|---|---|
| | 14 | 15 | 16 | 17 | 18 | 19 | 20 | 21 | 22 | 23 | 24 | 25 | 26 | 27 | 28 |
| Echinochloa crus-galli | 5 | 5 | 5 | 5 | 5 | 5 | 5 | 5 | 5 | 5 | 5 | 5 | 5 | 5 | 5 |
| Cyperus iria | 5 | 5 | 5 | 5 | 4 | 5 | 5 | 5 | 5 | 5 | 4 | 5 | 5 | 5 | 5 |
| Bidens pilosa | 5 | 5 | 5 | 5 | 5 | 5 | 5 | 5 | 5 | 5 | 5 | 5 | 5 | 5 | 5 |
| Setaria viridis | 5 | 5 | 5 | 5 | 5 | 5 | 5 | 5 | 5 | 5 | 5 | 5 | 5 | 5 | 5 |
| Solanum nigrum | 5 | 5 | 5 | 5 | 5 | 5 | 5 | 5 | 5 | 5 | 5 | 5 | 5 | 5 | 5 |
| Matricaria chamomilla | 5 | 4 | 4 | 5 | 4 | 4 | 5 | 5 | 5 | 5 | 5 | 5 | 5 | 5 | 5 |
| Amaranthus retyofiexus | 5 | 5 | 5 | 5 | 5 | 5 | 5 | 5 | 5 | 5 | 5 | 5 | 5 | 5 | 5 |
| Triticum aestivum | 0 | 0 | 0 | 0 | 0 | 0 | 0 | 0 | 0 | 0 | 0 | 0 | 0 | 0 | 0 |
| Zea mays | 0 | 0 | 0 | 0 | 0 | 0 | 0 | 0 | 1 | 1 | 0 | 1 | 1 | 1 | 1 |

(Note)
*The compound represented by No. corresponds to the compound of the same No. which is represented by the general formula (V) according to the present invention.

What is claimed is:

1. A benzyl ether compound represented by the formula (I):

(I)

wherein R represents a branched alkyl group of 5 to 8 carbon atoms, a cycloalkyl group of 4 to 8 carbon atoms, an alkyl group of 1 to 3 carbon atoms having an alicyclic group of 3 to 7 carbon atoms, an aralkyl group of 7 to 9 carbon atoms, an alkyl group of 2 to 4 carbon atoms having an alkoxy group of 1 to 4 carbon atoms, an alkenyl group of 3 to 6 carbon atoms, a straight-chain alkyl group of 2 to 8 carbon atoms which has been substituted by 1 to 15 fluorine atoms, or a branched alkyl group of 3 to 8 carbon atoms which had been substituted by 1 to 15 fluorine atoms, and X represents a nitro group or an amino group, provided that when X is a nitro group, R is neither an aralkyl group nor an ethyl group substituted by fluorine atoms.

2. A compound according to claim 1, wherein R is a branched alkyl group of 5 and 6 carbon atoms, an alkyl group of 1 to 2 carbon atoms having an alicyclic group of 3 to 6 carbon atoms, an aralkyl group of 7 carbon atoms, an alkyl group of 2 carbon atoms having an alkoxy group of 4 carbon atoms, an alkenyl group of 3 to 6 carbon atoms, a straight-chain alkyl group of 2 to 8 carbon atoms which has been substituted by 3 to 12 fluorine atoms, or a branched alkyl group of 3 to 8 carbon atoms which has been substituted by 3 to 12 fluorine atoms.

3. 1-(2-Methylbutoxy)methyl-3-nitrobenzene.
4. 1-(3-Methylbutoxy)methyl-3-nitrobenzene.
5. 1-(2,2-Dimethylpropoxy)methyl-3-nitrobenzene.

6. 1-([c]Cyclohexylmethoxy)methyl-3-nitrobenzene.
7. 1-(2,2,3,3,3-Pentafluoropropoxy)methyl-3-nitrobenzene.
8. 1-(2,2,3,4,4,4-Hexafluorobutoxy)methyl-3-nitrobenzene.
9. 1(2,2,3,3,4,4,4-Heptafluorobutoxy)methyl-3-nitrobenzene.
10. 1-(2,2,3,3,4,4,5,5-Octafluoropentoxy)methyl-3-nitrobenzene.
11. 3-[(2-Methylbutoxy)methyl]aniline.
12. 3-[(3-Methylbutoxy)methyl]aniline.
13. 3-[(2,2-Dimethylpropoxy)methyl]aniline.
14. 3-[(Cyclohexylmethoxy)methyl]aniline.
15. 3-[(2,2,2-Trifluoroethoxy)methyl]aniline.
16. 3-[(2,2,3,3,3Pentafluoropropoxy)methyl]aniline.
17. 3-[(2,2,3,4,4,4-Hexafluorobutoxy)methyl]aniline.
18. 1-(2,2,3,3,4,4,4-Heptafluorobutoxy)methyl]aniline.
19. 3-](2,2,3,3,4,4,5,5-[octafluoropentoxy)methyl]aniline.

* * * * *

UNITED STATES PATENT AND TRADEMARK OFFICE
CERTIFICATE OF CORRECTION

PATENT NO. : 5,001,275

DATED : March 19, 1991

INVENTOR(S) : Shida, et al.

It is certified that error appears in the above-identified patent and that said Letters Patent is hereby corrected as shown below:

On the title page, after "[22] Filed:   Nov. 7, 1989
insert --Related U.S. Application Data
[63] Continuation of Ser. No. 042,164, Apr. 24, 1987, abandoned.--

Col. 21, line 1:
In claim 6, "1-([c]Cyclohexylmethoxy)" should read --1-(Cyclohexylmethoxy)--.

Col. 21, line 6:
In claim 9, "1(2,2,3,3,4,4,4-Heptafluorobutoxy)" should read --1-(2,2,3,3,4,4,4-Heptafluorobutoxy)--.

Col. 22, line 5:
In claim 16, "3-[(2,2,3,3,3Pentafluoropropoxy)" should read --3-[(2,2,3,3,3-Pentafluoropropoxy)--.

Col. 22, line 7:
In claim 18, "1-(2,2,3,3,4,4,4-Heptafluorobutoxy)" should read --3-[(2,2,3,3,4,4,4-Heptafluorobutoxy)--.

Col. 22, line 9:
In claim 19, "3-](2,2,3,3,4,4,5,5-[octafluoropentoxy)" should read --3-[(2,2,3,3,4,4,5,5-Octafluoropentoxy)--.

Signed and Sealed this

Nineteenth Day of January, 1993

Attest:

DOUGLAS B. COMER

Attesting Officer

Acting Commissioner of Patents and Trademarks